US00PP27625P3

(12) United States Plant Patent
Kobelt

(10) Patent No.: US PP27,625 P3
(45) Date of Patent: Jan. 31, 2017

(54) APPLE TREE NAMED 'LURECHILD'

(50) Latin Name: *Malus domestica*
Varietal Denomination: Lurechild

(71) Applicant: Lubera AG, Buchs (CH)

(72) Inventor: Markus Kobelt, Buchs (CH)

(73) Assignee: Lubera AG, Buchs (CH)

( * ) Notice: Subject to any disclaimer, the term of this patent is extended or adjusted under 35 U.S.C. 154(b) by 73 days.

(21) Appl. No.: 14/544,111

(22) Filed: Nov. 25, 2014

(65) Prior Publication Data

US 2016/0150695 P1 May 26, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

*Primary Examiner* — Kent L Bell
(74) *Attorney, Agent, or Firm* — The Webb Law Firm

(57) ABSTRACT

A new and distinct *Malus domestica* plant that produces apples having a red flesh color and good eating quality.

9 Drawing Sheets

Botanical classification: *Malus domestica.*
Varietal denomination: 'Lurechild'.

BACKGROUND OF THE INVENTION

The present invention comprises a new and distinct cultivar of apple tree botanically classified as *Malus domestica* and known by the varietal name 'Lurechild'. The new variety was discovered in September of 2006 in Buchs, Switzerland. The new variety is the result of planned breeding program, in which *Malus domestica* 'LubA793' (female parent, unpatented) was crossed with *Malus domestica* 'LubA264' (male parent, unpatented). The purpose of the breeding program was to develop red-fleshed apples having an improved eating quality and scab resistance. The new variety exhibits similar sugar content, size, and scab resistance to its female parent, but is higher in acidity and has a red flesh color. The new variety exhibits similar red flesh and level of acidity to its male parent, but differs in eating quality. The red flesh color combined with good eating quality of 'Lurechild' distinguishes the new variety from other *Malus domestica* varieties known to the inventor. Its red flesh color, high sugar and acidity content, and scab resistance of the new variety are similar to *Malus domestica* 'Luresweet' (U.S. Plant patent application Ser. No. 14/544,112, concurrently applied-for herewith). However, 'Lurechild' has a much earlier harvest time than 'Luresweet'.

The new variety has been trial and field tested and has been found to retain its distinctive characteristics and remain true to type through successive propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
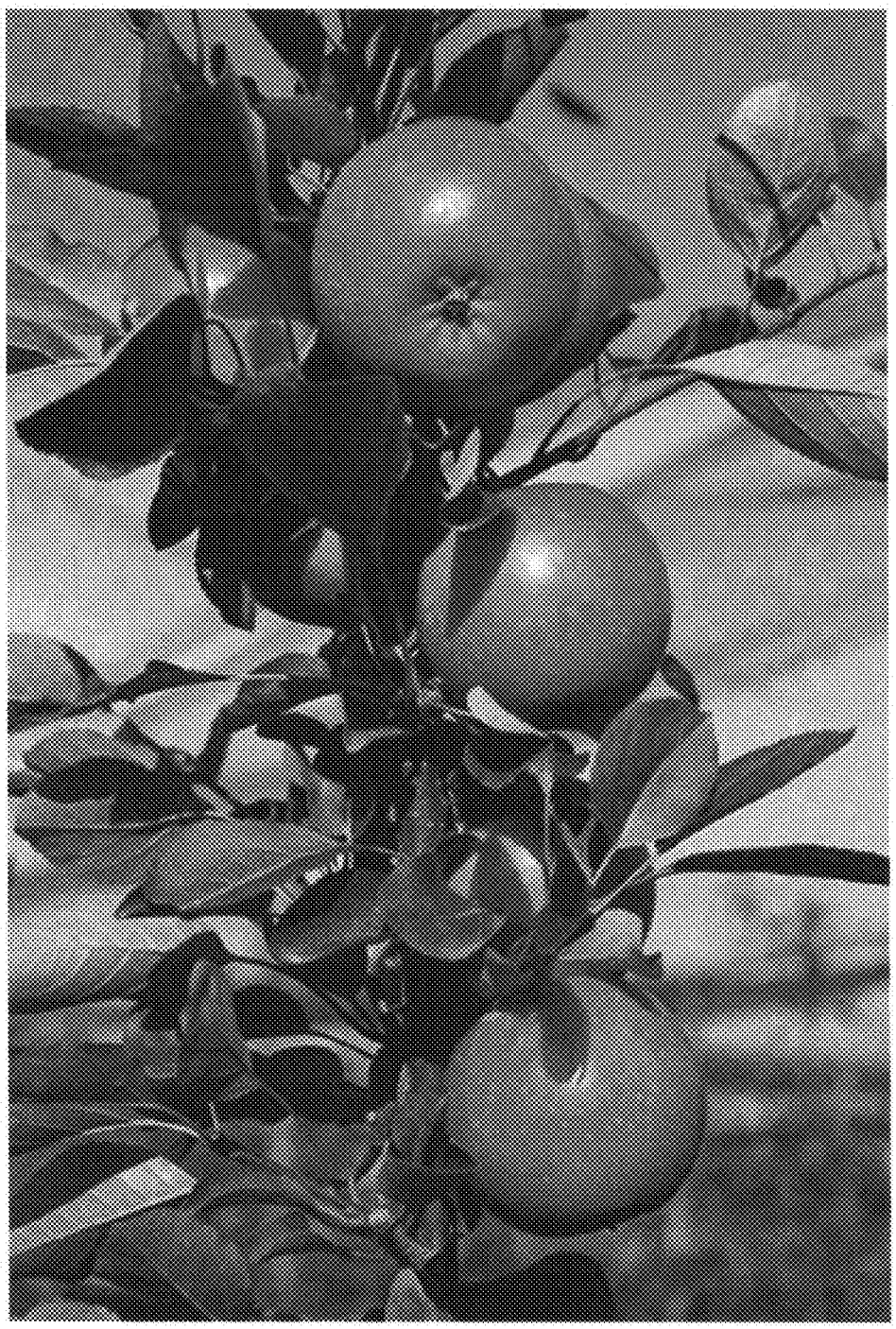
FIG. 1 is a close-up view of fruits of the new variety at maturity on the tree.
Figure 2:
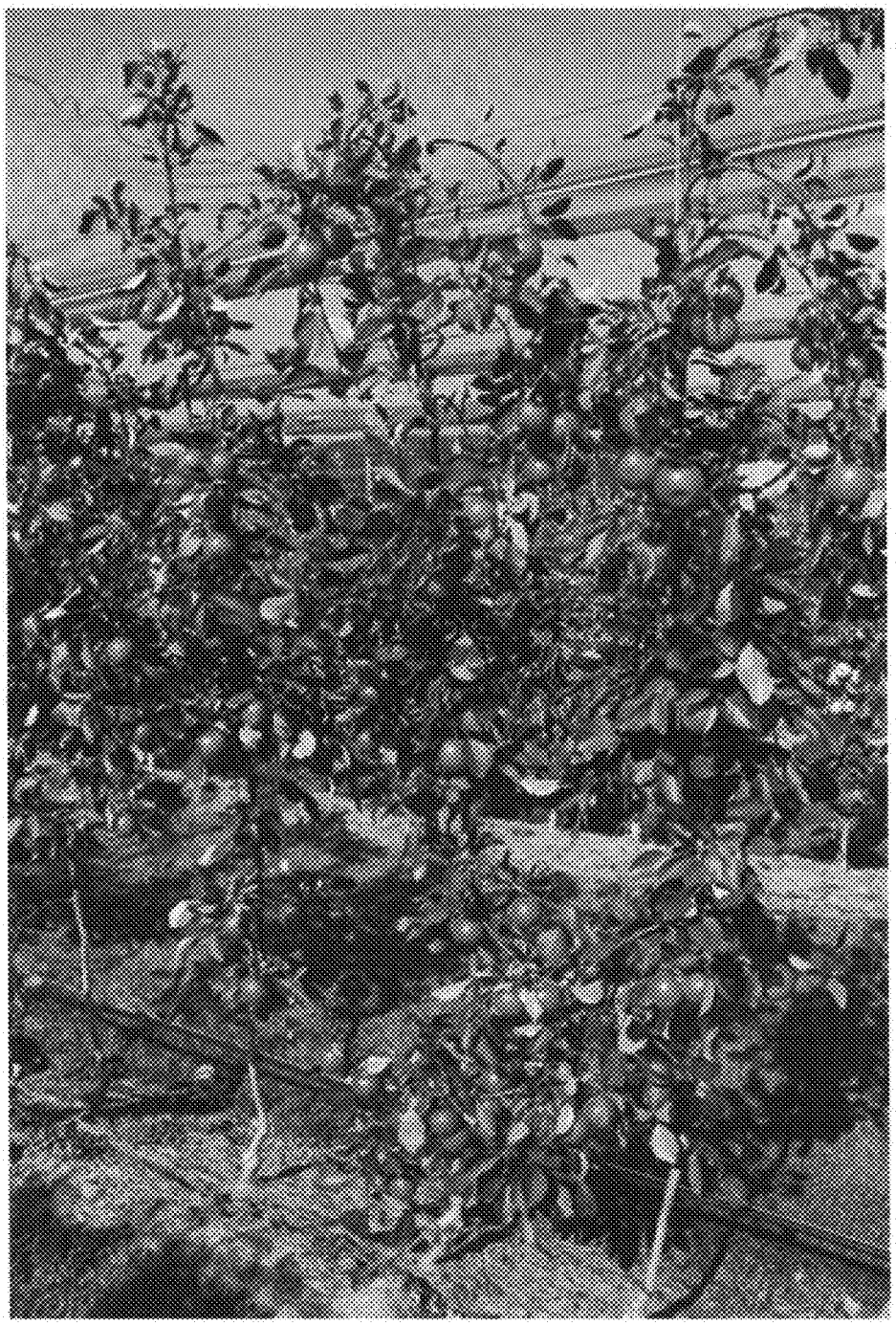
FIG. 2 shows fruits of the new variety at maturity on the tree.
Figure 3:
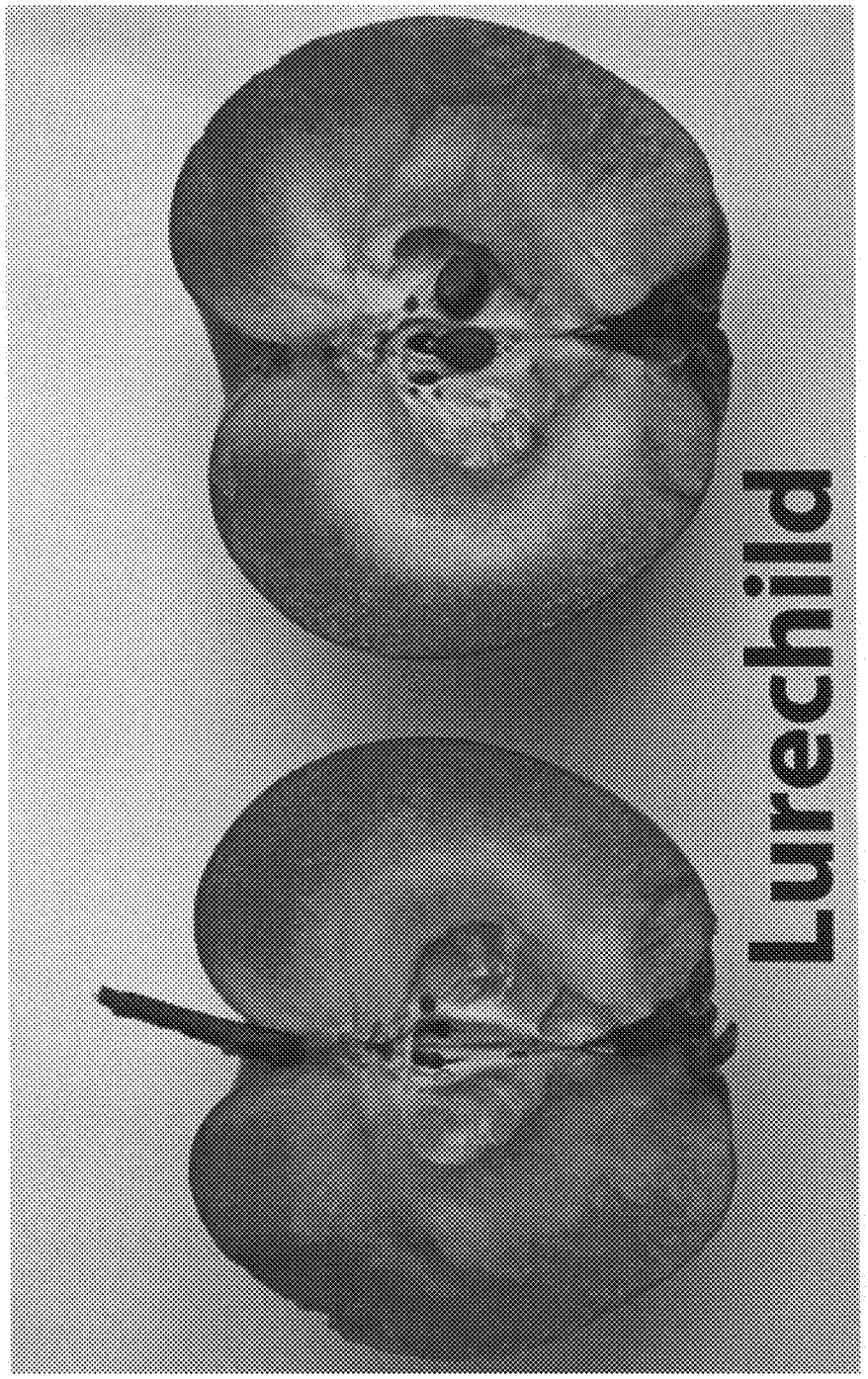
FIG. 3 is a longitudinal, cross-sectional view of a fruit of the new variety.
Figure 4:
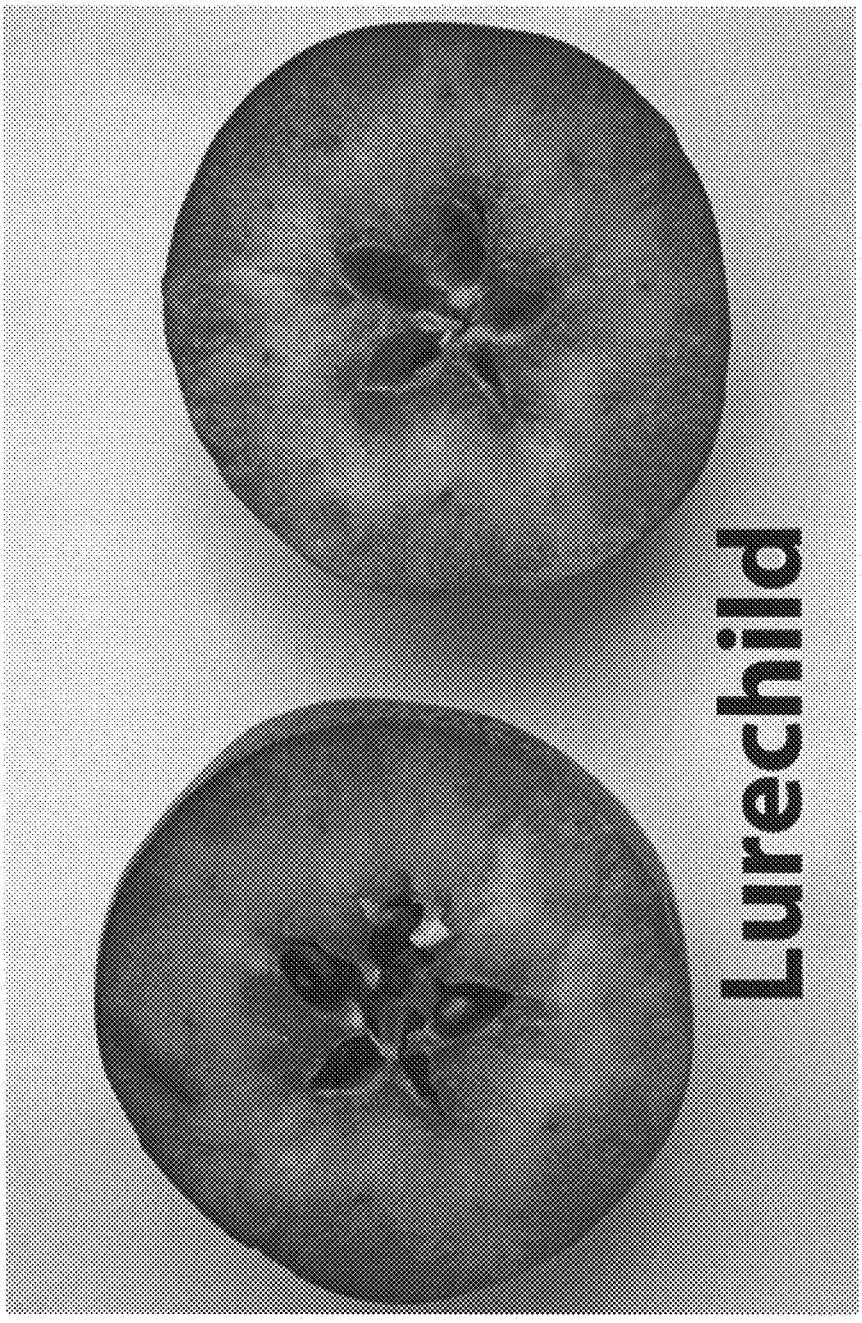
FIG. 4 is transverse, cross-sectional view of a fruit of the new variety.
Figure 5:
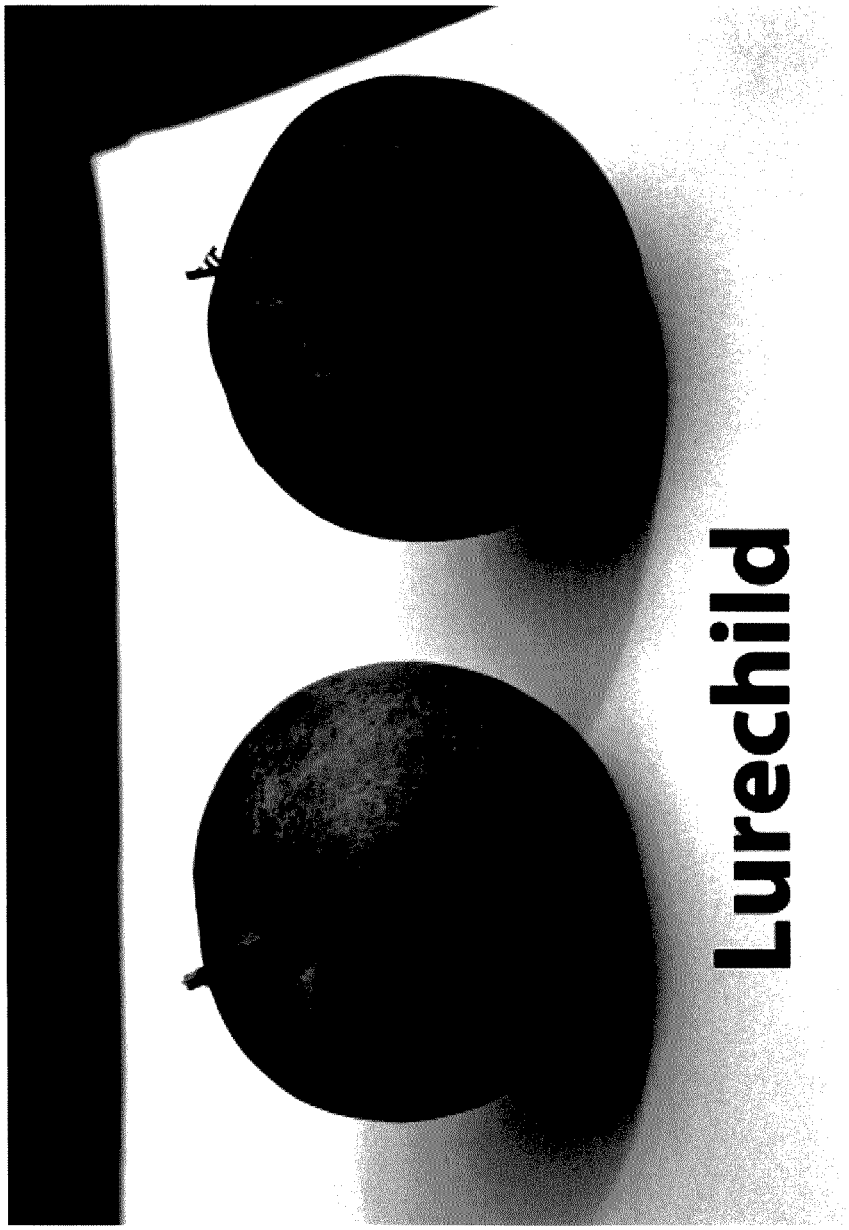
FIG. 5 shows the fruits of the new variety at maturity off the tree.
Figure 6:
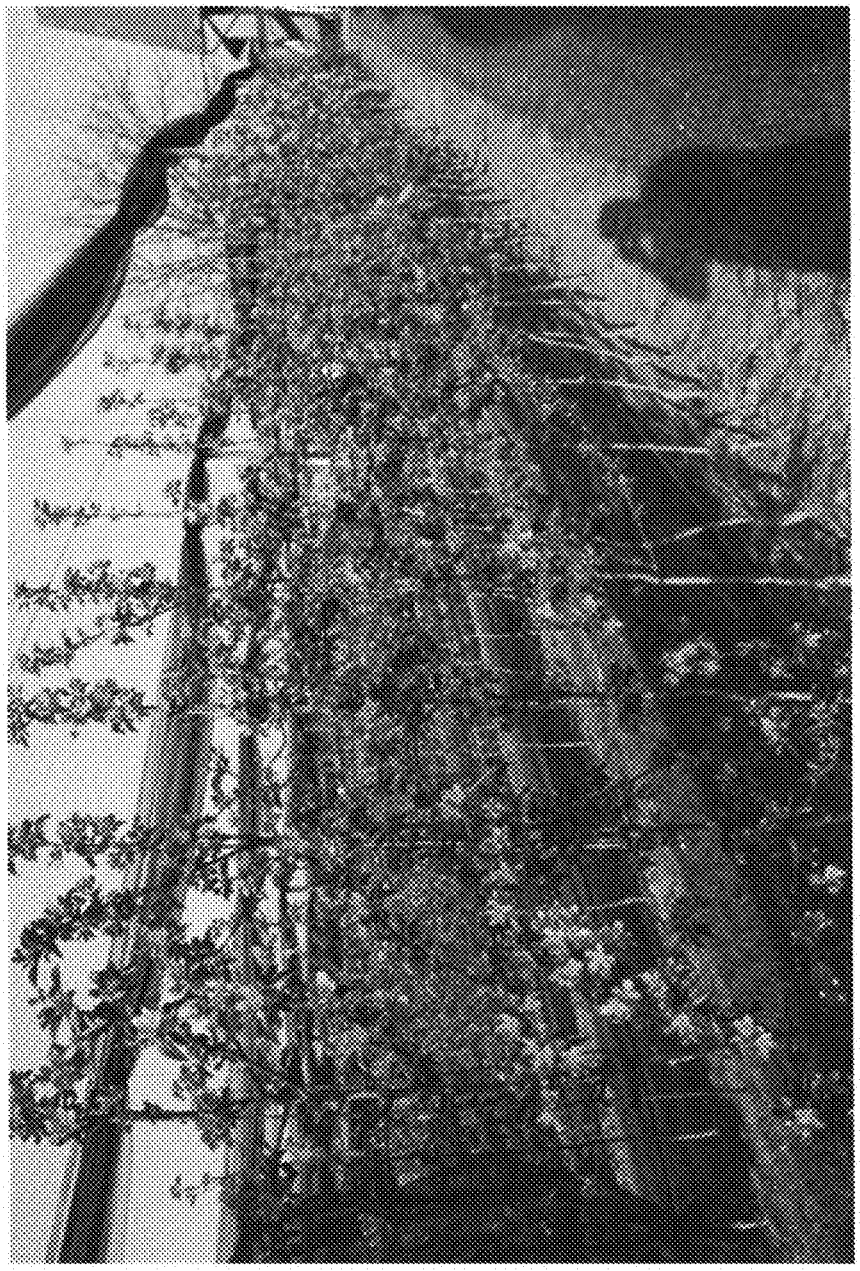
FIG. 6 shows buds and flowers of the new variety.
Figure 7:
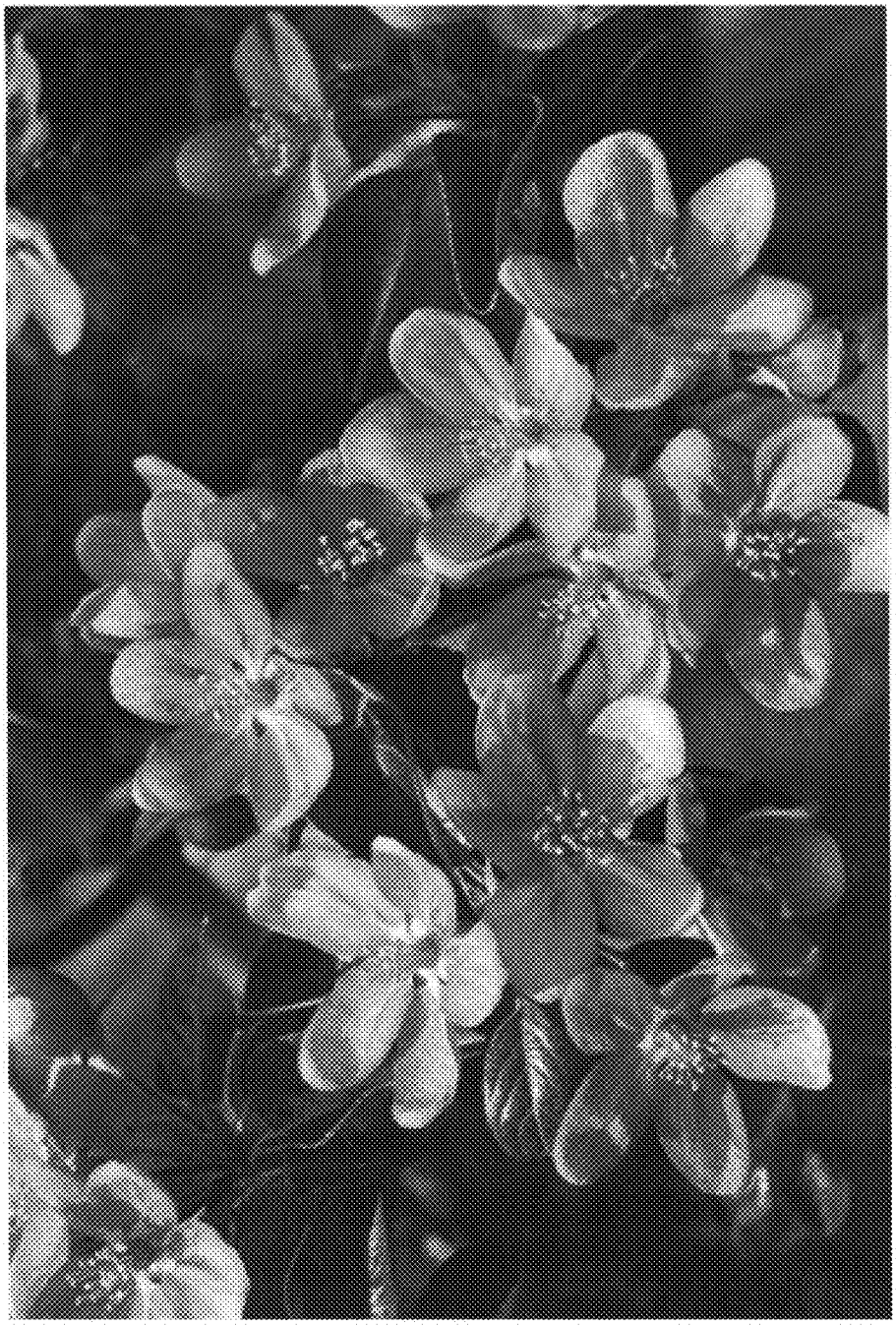
FIG. 7 is a close-up view of the flowers of the new variety.
Figure 8:
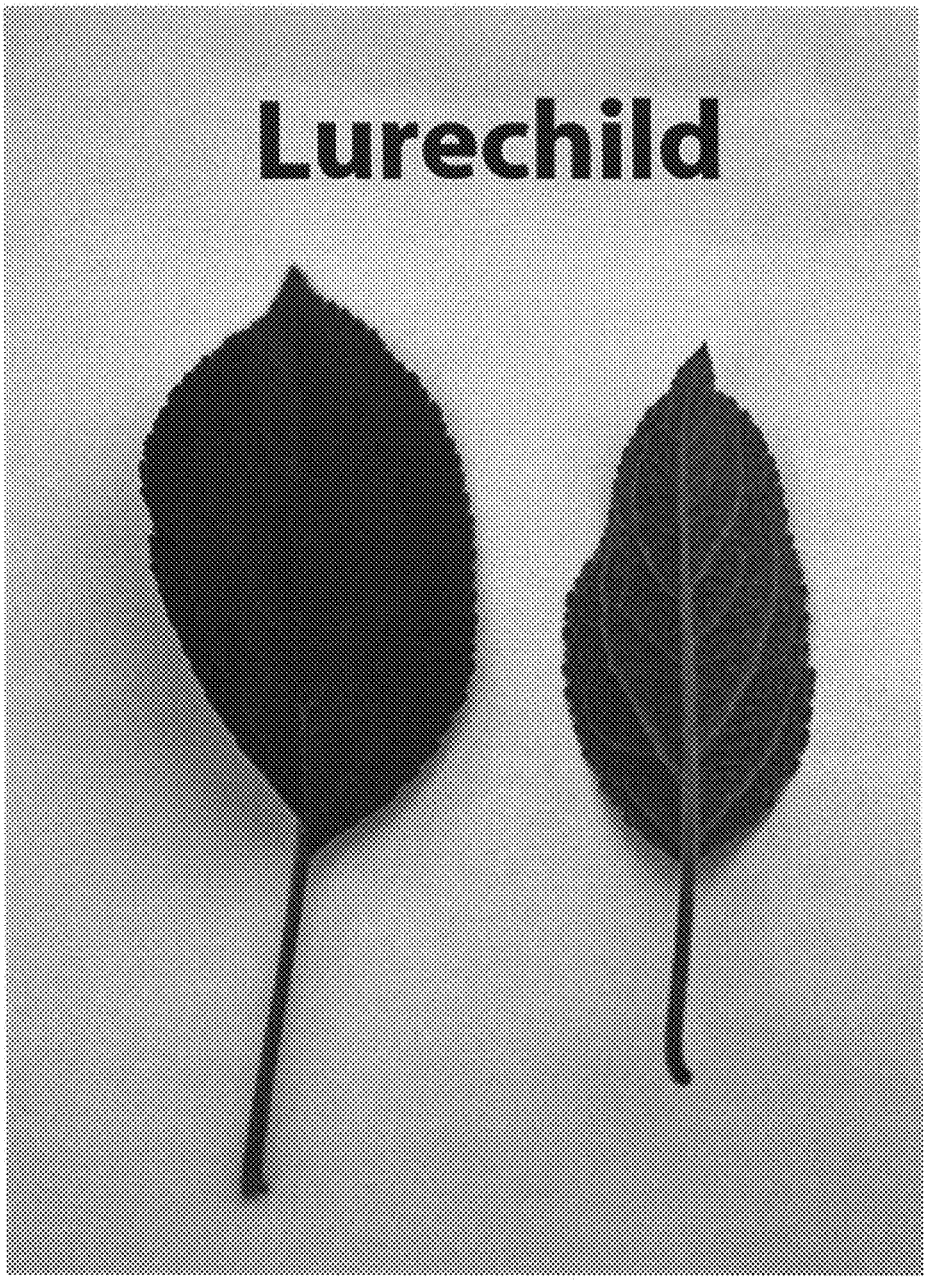
FIG. 8 shows upper and lower surfaces of young leaves of the new variety.
Figure 9:
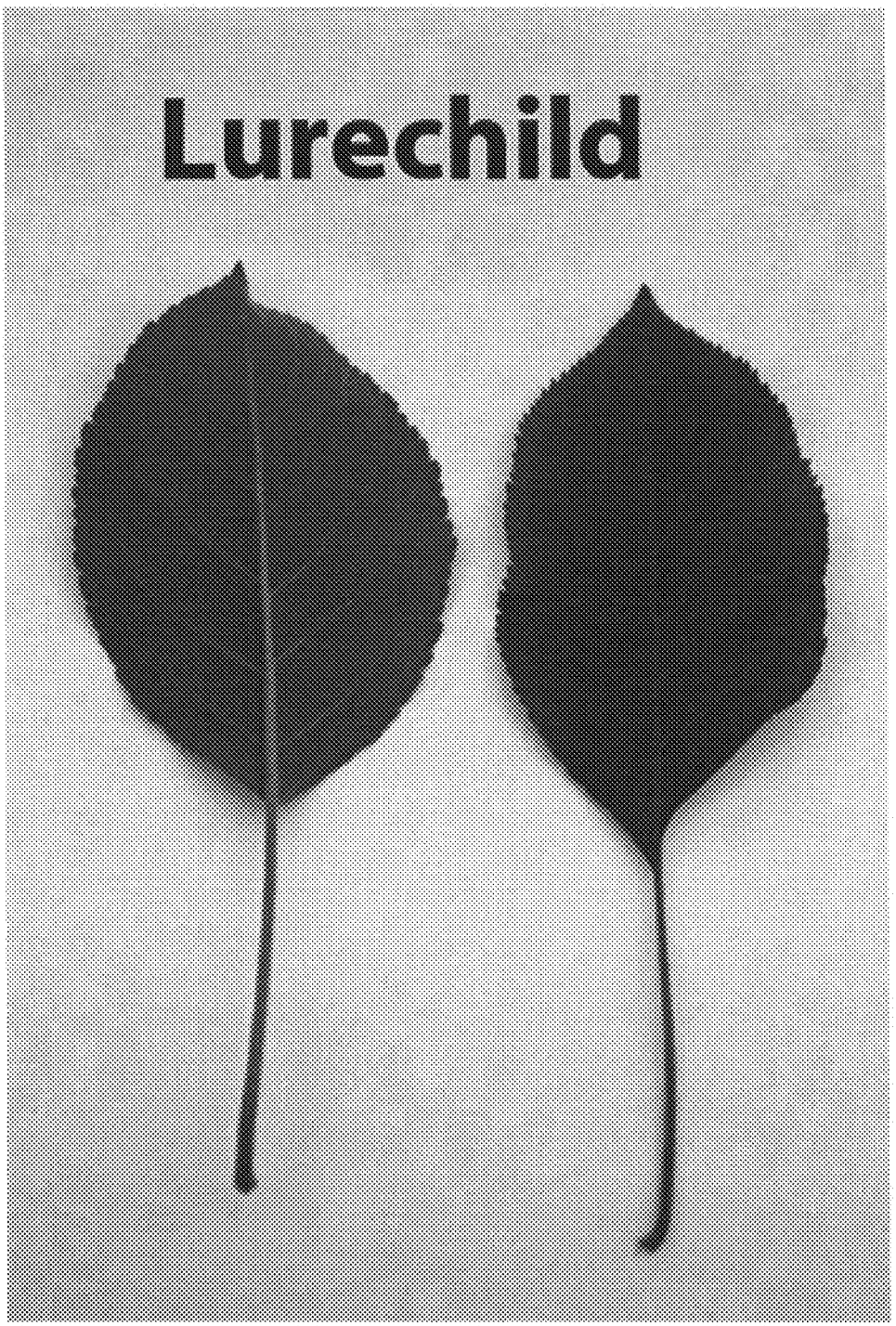
FIG. 9 shows upper and lower surfaces of mature leaves of the new variety.

The following detailed description sets forth the characteristics of the new cultivar. The data which defines these characteristics was collected by asexual reproductions carried out via grafting on *Malus domestica* rootstocks in the Spring of 2007 in Buchs, Switzerland. The new variety was grown in an apple orchard under standard apple tree conditions in Buchs, Switzerland. The color readings were taken in natural daylight without direct sunlight. Color references are primarily to The 2007 R.H.S. Colour Chart of The Royal Horticultural Society of London.

TREE

Age: 4 years.
Size: 2.2×0.5 m.
Spread: 3.2×0.5 m.
Average production: 7 kg per tree in a typical growing season.
Vigor: Weak.
Growth type: Ramified; spreading.
Trunk:
*Size*.—Average of 15.0 mm in diameter when measured 70 cm above the soil.
*Surface texture*.—Smooth.
*Bark color*.—177A.

*Lenticels*.—Length: 1.0-1.5 mm. Width: 0.5-0.7 mm. Color: 164C. Density: High.

Branches:

*Diameter*.—Average of 6.5 mm.

*Length*.—Average of 35 cm.

*Color*.—200B.

*Surface texture*.—Smooth, with absent or very weak pubescence at the distal half of shoots.

*Average angle*.—45°.

*Internode length*.—Medium; average of 2 cm.

*Lenticels*.—Length: 0.5-1.0 mm. Width: 0.2-0.6 mm. Shape: Oval to round. Density: High. Color: 159B.

Leaves:

*Length*.—11.0-12.0 cm.

*Width*.—7.0-9.0 cm.

*Shape*.—Oblong to oval.

*Apex*.—Pointed.

*Base*.—Flat; V-shaped.

*Margin*.—Finely crenate.

*Texture*.—Leathery with a slight shine.

*Pubescence*.—Upper surface: Absent. Lower surface: Weak.

*Color*.—Young leaves: Upper surface: 187A. Lower surface: 147C. Mature leaves: Upper surface: N137B. Lower surface: 147B.

*Petiole*.—Shape, when viewed in cross-section: Slightly crenate. Length: 2.5-3.0 cm. Diameter: 2.0 mm. Color: 187B.

*Veins*.—Venation type: Net-like. Color: Upper surface: 185B to 185C. Lower surface: 185C.

Flowers:

*Buds*.—Pedicels: Length: 25.0-27.0 mm. Diameter: 2.0 mm. Color: 184A. Bud (terminal): Length: 8.0 mm. Width: 4.0 mm. Color: 60A.

*Blooming time*.—From the middle to the end of April in Buchs, Switzerland.

*Blooming period*.—Approximately 15 days.

*Pollination requirements*.—Cross-pollination is necessary.

*Number of flowers per cluster*.—5 to 7.

*Fragrance*.—Slight.

*Petals*.—Number: 5. Length: 24.0-26.0 mm. Width: 16.0-17.0 mm. Shape: Oval. Apex: Rounded. Base: Rounded.

*Margin*.—Slightly wavy. Texture and appearance: Soft and fragile.

*Color*.—When opening: Upper surface: 60D. Lower surface: 60C. When fully opened: Upper surface: 73A. Lower surface: 73A.

*Sepals*.—Shape: Pointed. Apex: Pointed.

*Margin*.—Entire. Texture: Soft pubescence present. Length: 8.0 mm. Width: 4.0 mm. Color: Upper surface: 138C. Lower surface: 180B.

*Stamens*.—Number (per flower): 19. Filament length: 9.0-12.0 mm.

*Anthers*.—Average number per flower: 19. Shape: Oval to oblong. Length: 2.5 mm. Color: Yellowish.

*Pollen*.—Color: Yellowish.

*Pistils*.—Average number per flower: 5. Length: 14.0 mm. Color: 63C.

*Style*.—Length: 8.0-9.0 mm. Color: 63B to 63C.

*Stigma*.—Shape: Round. Color: 151B.

Fruit:

*Date of picking*.—September 10$^{th}$ to September 15$^{th}$.

*Average weight per fruit*.—150 g.

*Average number of fruits per cluster*.—3 to 4.

*Size*.—Axial diameter: 55.0-60.0 mm. Transverse diameter: 70.0-75.0 mm.

*Form*.—Roundish; oblong at top and bottom.

*Cavity*.—Acute, with medium depth (5 mm) and breadth (18 mm).

*Basin*.—Regular; ribbed; shallow-medium depth (7 mm); medium width (21 mm).

*Calyx*.—Half open.

Skin:

*Thickness*.—Medium.

*Texture*.—Smooth.

*Color*.—185A.

*Ground color*.—None.

Flesh:

*Color*.—46B.

*Texture*.—Firm.

*Eating quality*.—Very good; well-balanced sugar-acid content; berry-like taste; very juicy; Brix measurement of 14.5.

Core:

*Bundle area*.—White; clasping.

*Calyx tube*.—Conical; 7.0 mm from tube to shoulder.

*Styles*.—Closed.

*Stamens*.—Medium; inferior ovary.

*Seed cells*.—Average number per fruit: 5. Wall: Open. Depth: 11.0 mm. Breadth: 6.0-7.0 mm.

Seeds:

*Number perfect*.—16.

*Number in one cell*.—3.

*Length*.—9.0 mm.

*Breadth*.—4.0 mm.

*Form*.—Oval and pointed.

*Color*.—177A.

Stem:

*Length*.—28.0-30.0 mm.

*Width*.—3.0 mm.

*Color*.—183A.

Use: Table or dessert fruit.

Shipping quality: No bruising with normal handling.

Keeping quality: 3 months in a normal, cool storage area, but very sensitive to deep storage temperatures below 4-5° C.

Tree winter hardiness: Hardy to −18° C.

Bud winter hardiness: Hardy to −18° C.

Drought tolerance: Average.

Disease resistance: Resistant to scab.

I claim:

1. A new and distinct variety of *Malus domestica* tree substantially as shown and described.

* * * * *